(12) United States Patent
Zhou et al.

(10) Patent No.: US 8,705,030 B2
(45) Date of Patent: Apr. 22, 2014

(54) OPTICAL SAMPLE DETECTION SYSTEM AND SAMPLE ANALYSIS DEVICE

(75) Inventors: Yang Zhou, Shenzhen (CN); Zefei Jiang, Shenzhen (CN); Jinhong Qiu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 474 days.

(21) Appl. No.: 13/085,343

(22) Filed: Apr. 12, 2011

(65) Prior Publication Data

US 2011/0255086 A1 Oct. 20, 2011

(30) Foreign Application Priority Data

Apr. 14, 2010 (CN) .......................... 2010 1 0153067

(51) Int. Cl.
*G01J 3/28* (2006.01)

(52) U.S. Cl.
USPC .......................................................... 356/326

(58) Field of Classification Search
USPC ..................... 356/326–328; 359/227, 232
See application file for complete search history.

(56) References Cited

U.S. PATENT DOCUMENTS

| | | | | |
|---|---|---|---|---|
| 4,465,375 A | * | 8/1984 | Sakamoto | 356/434 |
| 4,888,484 A | * | 12/1989 | Harvey | 250/343 |
| 5,361,314 A | * | 11/1994 | Kopelman et al. | 385/12 |
| 5,680,209 A | * | 10/1997 | Machler | 356/319 |
| 6,157,454 A | * | 12/2000 | Wagner et al. | 356/407 |
| 6,768,095 B2 | * | 7/2004 | Niwa et al. | 250/216 |
| 2002/0024653 A1 | * | 2/2002 | Jung et al. | 356/73 |
| 2006/0181791 A1 | | 8/2006 | Van Beek et al. | |

FOREIGN PATENT DOCUMENTS

| | | |
|---|---|---|
| CN | 2482688 | 3/2002 |
| CN | 2674441 | 1/2005 |
| CN | 101073252 A | 11/2007 |
| CN | 200997027 | 12/2007 |
| CN | 101140224 | 3/2008 |
| CN | 201156091 | 11/2008 |
| CN | 101329251 A | 12/2008 |
| EP | 1632769 A1 | 8/2006 |
| JP | 9229855 | 9/1997 |
| WO | 2009016193 A1 | 2/2009 |

OTHER PUBLICATIONS

Feng, Jianwu and Zhiguo, Zhiguo, "Spectral of Partially Coherent Light Passing Through an Aperture-Lens Separation System," ACTA Photonica Sinica, Nov. 2002, pp. 1363-1364, vol. 31, No. 11, Science Press, online, http://www.cnki.net.

* cited by examiner

*Primary Examiner* — Kara E Geisel
(74) *Attorney, Agent, or Firm* — Kory D. Christensen; Stoel Rives LLP

(57) ABSTRACT

An optical sample detection system is provided, including a light source; a convergence projection component for converging light rays emitted by the light source; a sample accommodation component for accommodating a detected sample; a light beam collection component for receiving light rays carrying sample characteristic information and transmitted from the sample accommodation component; a light splitting component for splitting polychromatic lights collected by the light beam collection component into independent spectrums or spectral bands; and a photoelectric detection component for receiving optical signals of different wavelengths separated through the light splitting component.

10 Claims, 6 Drawing Sheets

OPTICAL SAMPLE DETECTION SYSTEM AND SAMPLE ANALYSIS DEVICE

CROSS-REFERENCE TO RELATED APPLICATION(S)

This application claims the benefit of Chinese Patent Application No. 201010153067.0, filed on Apr. 14, 2010, which is incorporated herein by reference in its entirety.

TECHNICAL FIELD

The following disclosure relates to optical sample detection.

DETAILED DESCRIPTION

Existing optical sample detection systems generally determine the ingredients in a sample by measuring a ratio of an incident light intensity to an emergent light intensity of a detected sample corresponding to different wavelengths. In order to ensure that light beams incident to a rear signal detection system carry correct information of the sample, the optical system is usually designed to ensured that light spots incident to the sample totally fall into the sample.

Figure 1:
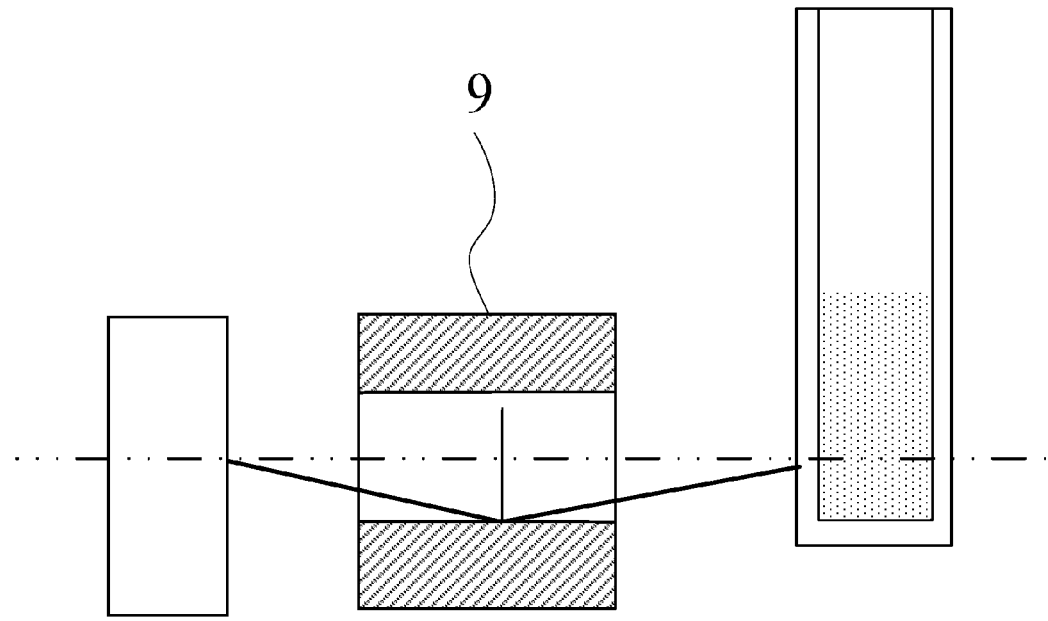
FIG. 1 illustrates an existing sample detection light path having a cylindrical stray light reduction structure.
Figure 2:
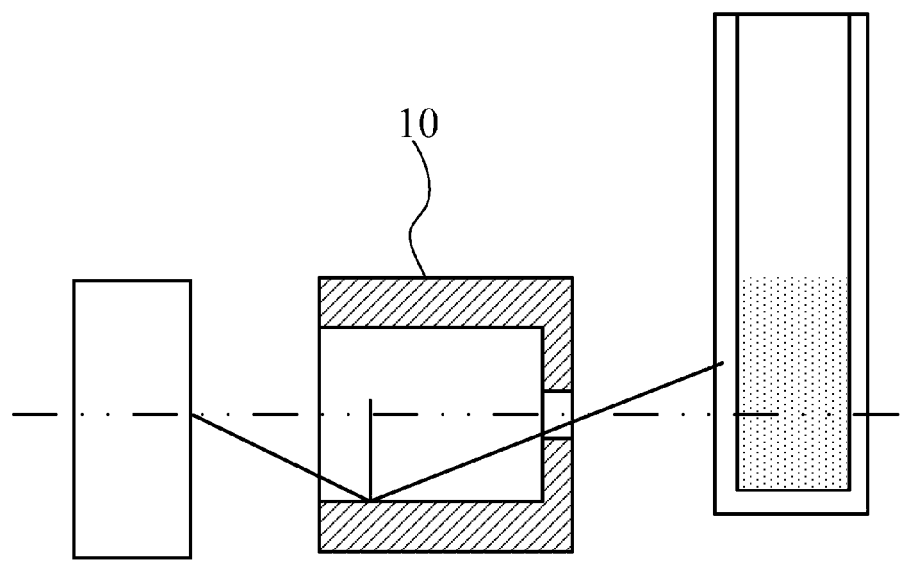
FIG. 2 illustrates an existing sample detection light path having a stepped stray light reduction structure.

In existing optical sample detection systems, generally an optical stop structure with suitable aperture is employed to ensure that the sizes of light spots irradiated to the sample satisfy use requirements. FIG. 1 illustrates a sample detection light path having an optical stop 9 of an existing cylindrical through-hole structure, and FIG. 2 illustrates a sample detection light path having an optical stop 10 of an existing stepped hole structure. When one of the two optical stops is used, part of the light beams are obstructed by the optical stop due to limitations of the optical stop on the light beams. If reflected light rays generated by the obstructed light beams are incident to a rear optical system, the reflected light rays acting as stray light possibly influence the size of a practical light spot, and then influence a measurement result of the optical system, thereby influencing sample analysis precision.

In order to overcome these problems, the present disclosure provides an optical sample detection system and a sample analysis device, in which the optical sample detection system includes a light source; a convergence projection component configured for converging light rays emitted by the light source; a sample accommodation component configured for accommodating a detected sample; a light beam collection component configured for receiving light rays carrying sample information and transmitted from the sample accommodation component; a light splitting component configured for splitting polychromatic lights collected by the light beam collection component into independent spectrums or spectral bands; and a photoelectric detection component configured for receiving optical signals of different wavelengths separated through the light splitting component, in which the convergence projection component further includes an optical stop, in which included angles between directions of at least a part of the normals and a direction of an optical axis of the optical system are larger than 90°, the direction of the normal refers to a direction pointing to an inside of the optical stop from the surface of the optical stop, and the direction of the optical axis refers to a light beam propagation direction.

Advantageously, by controlling a shape of an internal surface of an optical stop, in an internal surface of the optical stop, included angles between directions of at least a part of the normals and a direction of an optical axis of the optical sample detection system are larger than 90°, so that a size of a light spot is limited, and a stray light is effectively controlled, thereby reducing influences of the stray light on a detection result of a rear optical system, and increasing a sample analysis precision.

In one embodiment, an optical sample detection system includes a light source; a convergence projection component for converging light rays emitted by the light source; a sample accommodation component for accommodating a detected sample; a light beam collection component for receiving light rays carrying sample information and transmitted from the sample accommodation component; a light splitting component for splitting polychromatic lights collected by the light beam collection component into independent spectrums or spectral bands; and a photoelectric detection component for receiving optical signals of different wavelengths separated through the light splitting component. The convergence projection component further includes an optical stop, in an internal surface of the optical stop, wherein included angles between directions of at least a part of the normals and a direction of an optical axis of the optical system are larger than 90°, the direction of the normal refers to a direction pointing to an inside of the optical stop from the surface of the optical stop, and the direction of the optical axis refers to a light beam propagation direction. By controlling a shape of the internal surface of the optical stop, in the internal surface of the optical stop, the included angles between directions of at least a part of the normals and a direction of an optical axis of the optical system are larger than 90°, so that a size of a light spot is limited, and stray light is effectively controlled, thereby reducing influences of the stray light on the detection result of a rear optical system, and increasing the sample analysis precision. The stray light is limited only by controlling the direction of the light beam, thereby greatly reducing the cost.

Figure 3:
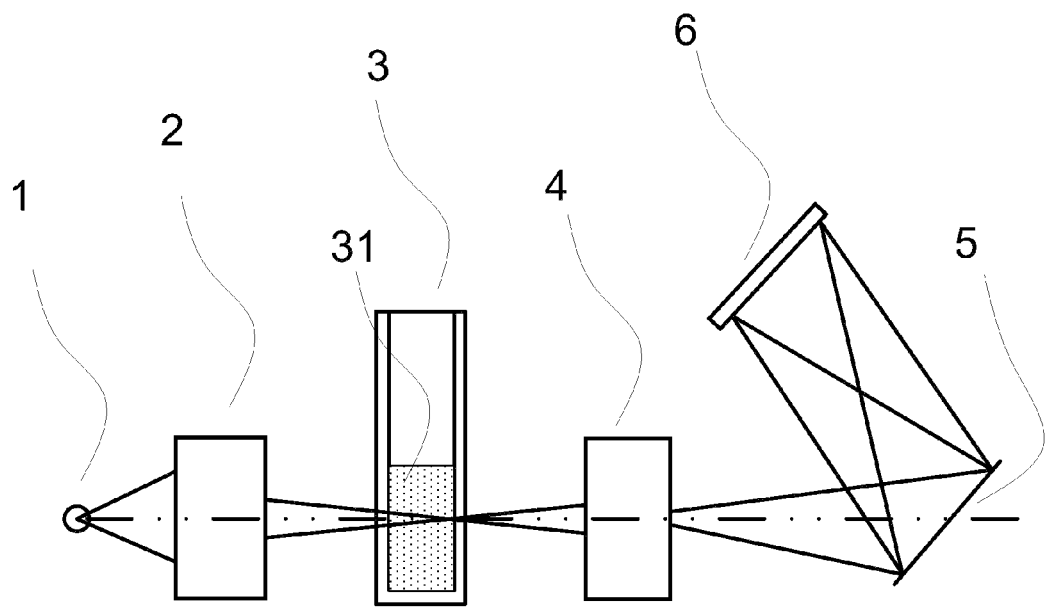
FIG. 3 illustrates an optical sample detection system.

Referring to FIG. 3, the optical sample detection system includes a light source 1, a convergence projection component 2, a sample accommodation component 3, a light beam collection component 4, a light splitting component 5, and a photoelectric detection component 6. The convergence projection component 2 is used for converging light rays emitted from the light source 1, and projecting the light rays to the sample accommodation component 3. The sample accommodation component 3 is used for accommodating a detected sample 31. The light beam collection component 4 is used for receiving light rays that are transmitted from the sample accommodation component 3 and contain sample information. The light splitting component 5 is used for splitting polychromatic lights collected by the light beam collection component 4 into independent spectrums or spectral bands. The photoelectric detection component 6 is used for receiving optical signals of different wavelengths separated through the light splitting component 5, and converting the optical signals into electrical signals, thereby detecting different ingredients of the sample. The light splitting component either may be located between the light beam collection component 4 and the photoelectric detection component 6, or may be located between the convergence projection component 2 and the sample accommodation component 3, or may be located inside the convergence projection component 2 to form a part of a front light splitting system.

Figure 4:
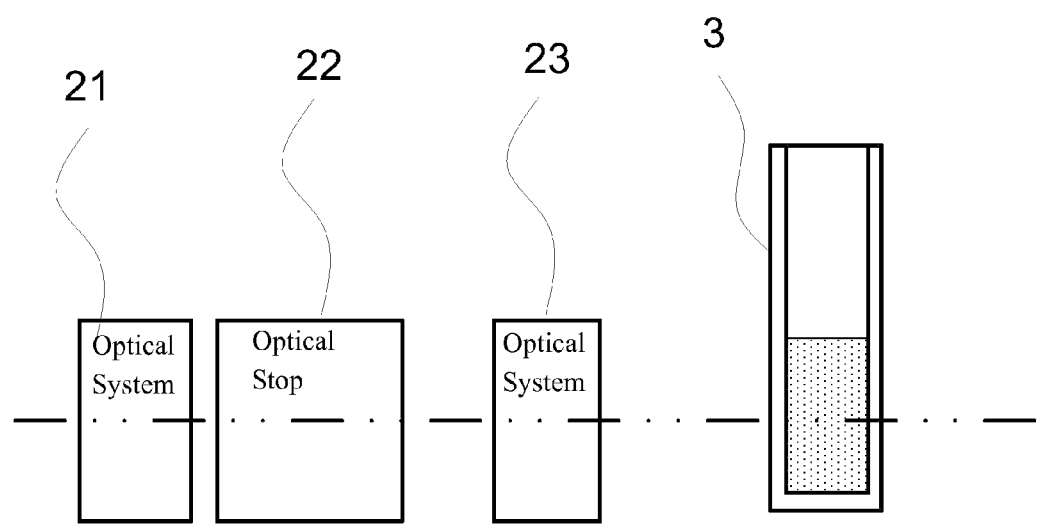
FIG. 4 illustrates an optical system of a convergence projection component.

Referring to FIG. 4, in one embodiment, the convergence projection component 2 is used for converging the light rays emitted by the light source 1, and projecting the light rays to the sample accommodation component 3. The sample accommodation component is used for accommodating the sample 31. Furthermore, a reagent may be added for sample detection, and the sample accommodation component is used for accommodating a reaction liquid of the sample and the reagent. The convergence projection component includes a front optical system 21, an optical stop 22 for stray light reduction, and a rear optical system 23. The front optical system 21 is used for converging optical energy emitted by the light source, as well as controlling incident energy of the light source according to practical needs. After being incident to an internal surface of the optical stop, the light rays are reflected and stray light rays are generated. Once the reflected light ray enters the rear photoelectric detection component 6, sample detection precision is influenced.

The optical stop 22 for stray light reduction is a special optical stop capable of constraining the stray light generated by the front system while being an optical stop for ensuring to control an aperture of an emergent light beam according to optical designing needs. The rear optical system 23 is used for projecting the light beam well adjusted through the front optical system 21 and the optical stop 22 for stray light reduction to the sample accommodation component 3. Both the front optical system 21 and the rear optical system 23 may be a single lens, or a lens group formed by a plurality of lenses, or may be a optical system formed by a lens group and a light beam control structure (such as optical stop). The convergence projection component 2 either may simultaneously include the front optical system 21 and the rear optical system 23, or may only include the front optical system 21, or may only include the rear optical system 23.

The convergence projection component further includes an optical stop, in an internal surface of the optical stop, wherein included angles between directions of at least the part of the normals and the direction of an optical axis of the optical system are larger than 90°, the direction of the normal refers to a direction pointing to an inside of the optical stop from the surface of the optical stop, and the direction of the optical axis refers to a light beam propagation direction. By controlling the shape of the internal surface of the optical stop, in the internal surface of the optical stop, the included angles between directions of at least the part of the normals and the direction of an optical axis of the optical system are larger than 90°, so that the size of the light spot is limited, and the stray light is effectively controlled, thereby reducing influences of the stray light on a detection result of a rear optical system, and increasing sample analysis precision.

In one embodiment, the internal surface of the optical stop of the optical sample detection system includes at least one tapered surface, and the direction of the normal at the tapered surface is deflected, so that the included angle between the emergent direction of the reflected stray light and the optical axis becomes larger, and the stray light deviates from the area of the detected sample, thereby increasing the sample detection precision.

Figure 5:
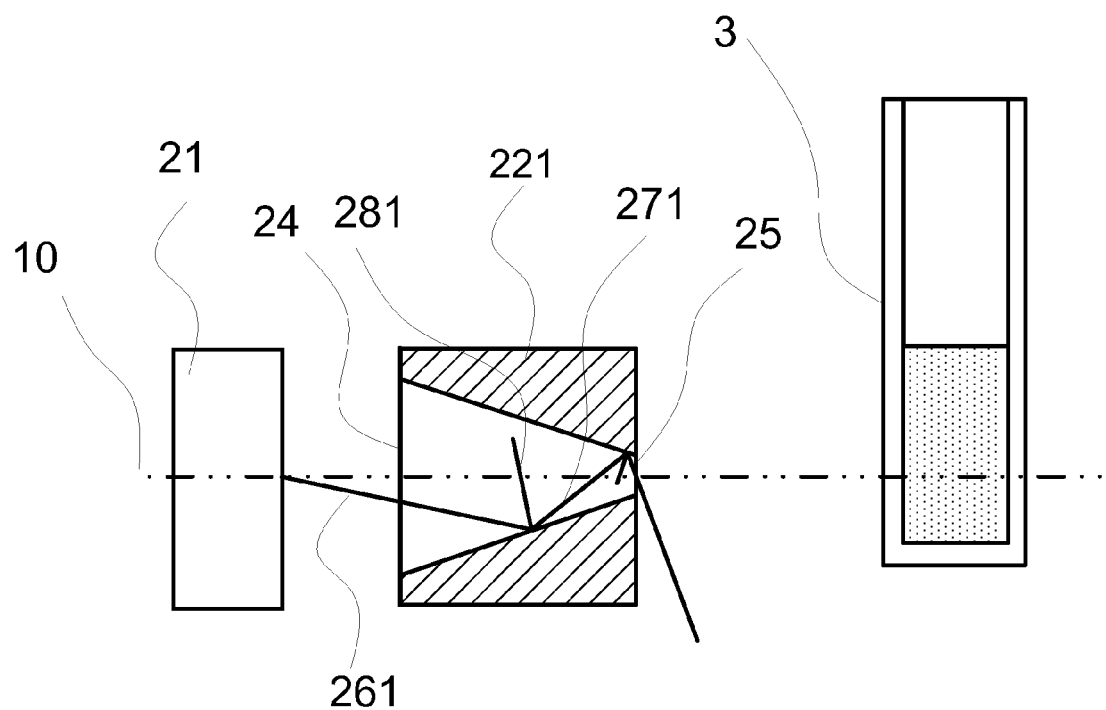
FIG. 5 illustrates an optical sample detection system.

FIG. 5 illustrates an embodiment of the optical sample detection system according to the present disclosure. An internal surface of an optical stop 221 for stray light reduction includes a round tapered surface. A front surface and a rear surface of the optical stop along a direction of an optical axis are respectively corresponding to a large hole 24 and a small hole 25. An emergent light rays of the front optical system 21 are incident from the large hole 24 of the optical stop for stray light reduction, and is emergent from the small hole 25 of the optical stop for stray light reduction. The large hole and the small hole are relative, if the front entrance hole of the optical stop is larger than the rear exit hole, the front entrance hole is called the large hole, and the rear exit hole is called the small hole. A light ray 261 emergent from the front optical system 21 is irradiated to the internal surface of the optical stop 221 for stray light reduction. Due to the reflection action of the surface, a reflected light ray 271 of the incident light ray 261 is emergent along a certain direction. According to the optical reflection law, the emergent direction of the reflected light ray 271 is associated with the included angle between the incident light ray 261 and a normal 281 of the reflection surface. Compared with the cylindrical optical stop or the stepped optical stop in the prior art, the internal surface of the optical stop is a round tapered surface, the incident light ray 261 is incident from the large hole 24 of the optical stop 221 for stray light reduction, and the normal 281 is vertical to the internal surface of the optical stop, so the included angle θ between the direction of the normal and the direction of the optical axis is larger than 90°.

Figure 6:
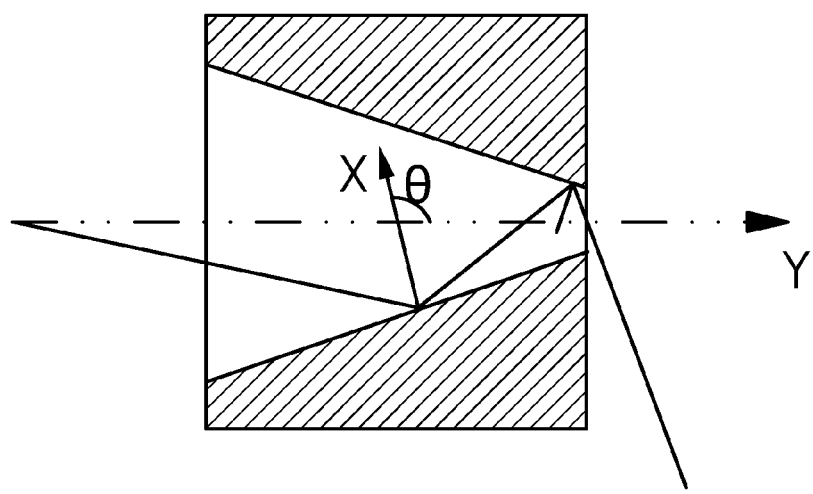
FIG. 6 is a schematic view of an included angle between a direction of a normal and a direction of an optical axis.

Referring to FIG. 6, the direction of the normal is defined as a direction pointing to the inside of the optical stop from the surface of the optical stop, such as Direction X in the drawing. The direction of the optical axis is defined as a light beam propagation direction, such as Direction Y in the drawing.

The included angle θ between the direction of the normal (X direction) and the direction of the optical axis (Y direction) is larger than 90°, so the included angle between the incident light ray 261 and the surface normal 281 of the reflection surface is smaller. According to the optical reflection law, the included angle between the reflected light ray 271 and the surface normal 281 is equal to the included angle between the incident light ray 261 and the surface normal 281 of the reflection surface, so the included angle between the emergent light ray 271 and the surface normal 281 of the reflection surface is also reduced accordingly.

Therefore, the included angle between the reflected light ray 271 and the optical axis 10 of the optical system is increased, that is, a deflection angle of the reflected light ray relative to the optical axis becomes larger. The reflected light ray 271 is reflected twice, and the deflection angle of the stray light emergent from the optical stop relative to the optical axis is further increased, so that the stray light emergent from the optical stop deviates from the sample, and cannot be incident to the rear optical system 23, thereby effectively controlling the emergent direction of the stray light, reducing the influences of the stray light on the rear photoelectric detection system, and increasing the sample detection precision.

Meanwhile, by controlling the shape of the surface of the optical stop compared with the cylindrical optical stop 9 or the stepped optical stop 10 (FIGS. 1 and 2, respectively), because the deflection angle of the light ray relative to the optical axis is increased, the incident light ray is reflected inside the optical stop many times. The surface of the optical stop is an opaque structure, and a majority of the energy of the incident light ray is scattered or absorbed during reflection every time, so the stray light is greatly reduced upon many times of reflection. Therefore, by increasing the reflection times of the stray light in the optical stop, the purposes of reducing the stray light and increasing the sample detection precision may also be achieved. In this way, by making the included angle θ between the direction of the normal (X direction) and the direction of the optical axis (Y direction) be larger than 90°, the emergent light ray of the light ray is controlled to deviate from the area of the detected sample, so that the sample detection precision may be increased; or the reflection times of the stray light in the optical stop is increased, so the energy of the reflected light ray may be weakened, thereby increasing the sample detection precision; or the stray light is both reduced and deflected from the area of the detected sample.

In conclusion, by controlling the shape of the internal surface of the optical stop, the emergent light ray corresponding to the light ray incident into the optical stop and reflected by the optical stop deviates from the area of the detected sample and/or the reflection times of the light ray incident to the optical stop and reflected by the optical stop is increased, so the optical energy of the reflected light ray is weakened, thereby effectively controlling the stray light, and increasing the sample detection precision. Moreover, the optical stop is manufactured simply, so as to effectively control the cost.

In one embodiment, the taper of the round tapered surface may also be further increased, the taper increase makes the included angle between the direction of the normal (X direction) and the direction of the optical axis (Y direction) be further increased, and then the angle between the incident light ray 261 and the surface normal 281 further becomes smaller, so that the angle between the reflected light ray 271 and the surface normal 281 further becomes smaller, and the included angle between the reflected light ray 271 and the optical axis 10 of the optical system further becomes larger. The reflected light ray deviates from the sample more easily, and cannot enter the rear optical system 23, so as to increase the sample detection precision. The included angle between the reflected light ray 271 and the optical axis 10 of the optical system further becomes larger, so the reflection times of the stray light in the optical stop 221 for stray light reduction becomes larger, and then the stray light ray is greatly weakened, so as to increase the sample detection precision.

According to the above embodiment, as long as the reflected light ray is avoided from falling into the detected area for sample detection, the stray light may be effectively controlled, so as to increase the sample detection precision. Meanwhile, the reflection times of the reflected light ray in the optical stop is increased, and the energy of the stray light may also be lost after being reflected in the optical stop 221 for stray light reduction many times, so that the stray light is incident to the rear optical system 23 as less as possible, and likewise the sample detection precision may also be increased. According to such a purpose, by controlling the shape of the optical stop, and then controlling the emergent direction of the reflected light ray, the emergent light ray of the light ray reflected by the internal surface of the optical stop may deviate from the sample and/or is reflected by the internal surface of the optical stop many times, so as to increase the sample detection precision.

The taper of the internal surface of the optical stop may be comprehensively considered according to the requirement of the minimal detection volume of the sample analysis device and optical parameters of the front and rear optical systems. The minimal detection volume refers to the minimal sample amount satisfying the requirement of the sample analysis test.

Generally, the size of the light spot projected on the sample accommodation component 3 is smaller than the area of cross-section of the minimal detection volume of perpendicular to the optical axis, and the smaller the minimal detection volume is, the smaller the requirement on the size of the light spot is. In the sample analysis device, the sample accommodation device is used for accommodating the sample.

Figure 7:
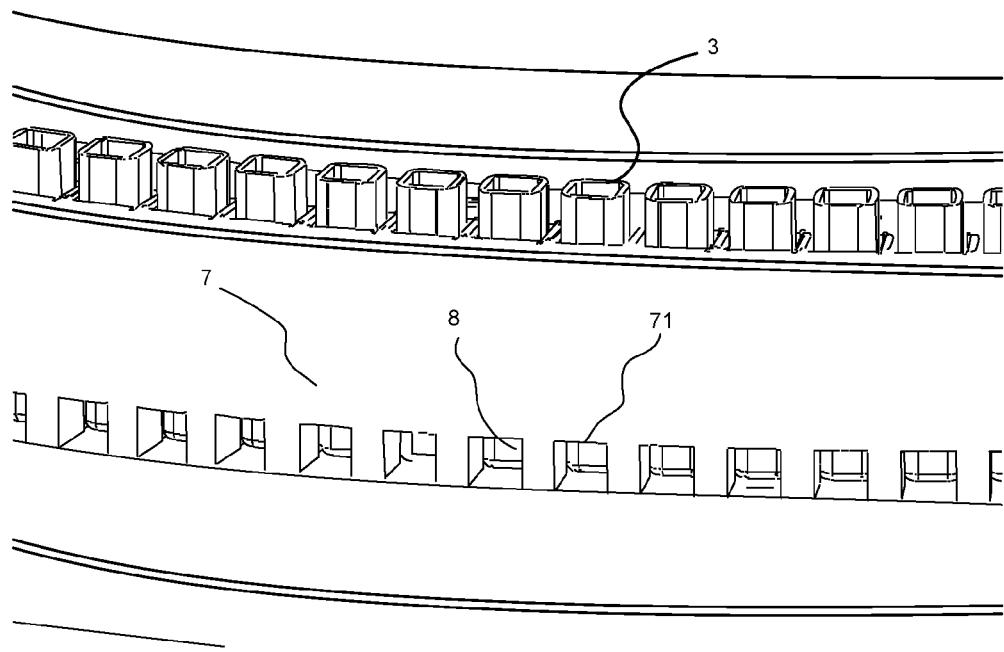
FIG. 7 is a drawing of a position relation between a reaction cuvette and a reaction wheel.

Further, for detection, the sample accommodation device further accommodates a reagent, and is used for accommodating a reaction liquid of the sample and the reagent, the sample accommodation device generally refers to a reaction cuvette, and the reaction cuvette is placed in a reaction wheel. FIG. 7 illustrates a drawing of a relation between the reaction cuvette and the reaction wheel. Several reaction cuvette mounting grooves are provided in the reaction wheel, the reaction cuvettes are mounted in the mounting grooves, and the reaction cuvettes accommodate a reaction liquid of the sample and the reagent. In order to make the reaction of the reaction liquid be complete, generally the reaction liquid further needs to be heated, so that a part of the reaction cuvette is obstructed by an edge 71 of the reaction wheel 7, the volume of the testable reaction liquid is further reduced, and only light passing windows 8 may be used for light passing to perform sample analysis. A part of the reaction liquid without being obstructed by the reaction wheel contains the area of the detected sample, and the area of the detected sample is designed by comprehensively considering various factors of detection.

After the incident light beam is incident to the optical stop for stray light reduction according to a certain aperture angle, the emergent light ray of the light ray reflected by the internal surface of the optical stop deviates from the area of the detected sample. By increasing the reflection times of the stray light in the optical stop, because the optical stop is made of an opaque material, the energy of the stray light may also be lost by being reflected in the optical stop 221 for stray light reduction many times, and cannot be incident to the rear optical system 23. Likewise the sample detection precision may also be increased. The shapes and the sizes of the apertures of the large hole 24 and the small hole 25 of the optical stop for stray light reduction are determined according to practical optical designing requirements.

Figure 8:
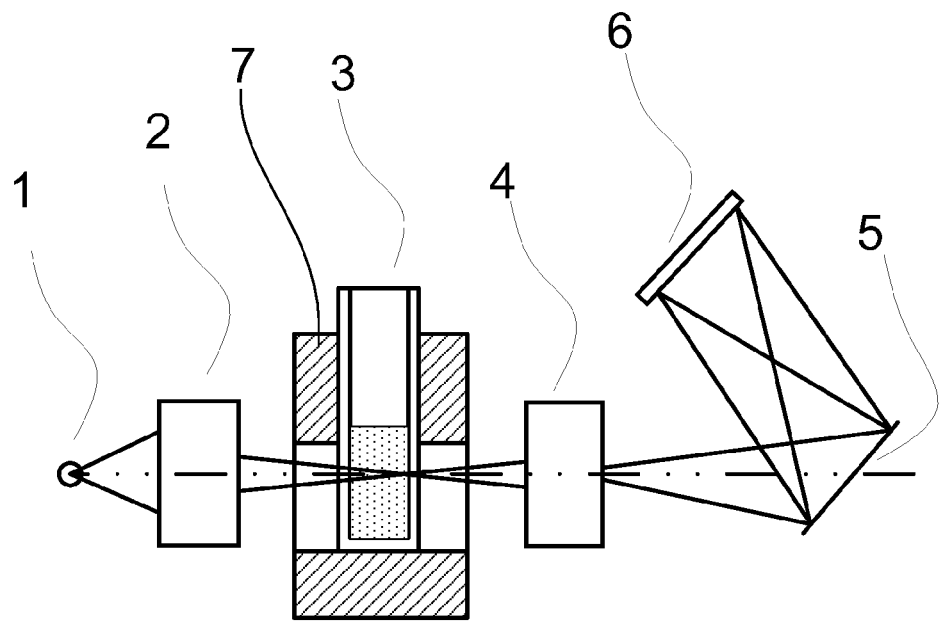
FIG. 8 illustrates a convergence projection component.

In one embodiment, as shown in FIG. 8, a part of the sample accommodation device 3 is obstructed by the reaction wheel 7, so only a part of the sample accommodation device 3 may be used for detection. At the same time of ensuring to limit the size of the light spot, by controlling the internal shape of the optical stop, the stray light is effectively controlled, thereby reducing the influences of the stray light on the detection result of the rear optical system, and increasing the sample analysis precision; and the optical stop is manufactured simply, so as to greatly reduce the cost.

The internal surface of the optical stop at least includes one tapered surface, and may further include surfaces in another shape besides the tapered surface; besides a round tapered surface, the internal surface of the optical stop for stray light reduction may further adopt a pyramidal surface, or a hybrid surface of the round tapered surface and the pyramidal surface, or any other deformed tapered surfaces. As long as the light ray of the emergent stray light reflected by the internal surface of the optical stop deviates from the detected sample, or scattered and absorbed upon many times of reflection by designing the reasonable shape of the internal surface of the optical stop and then controlling the direction of the reflected stray light, the sample detection precision may be increased.

Figure 9:
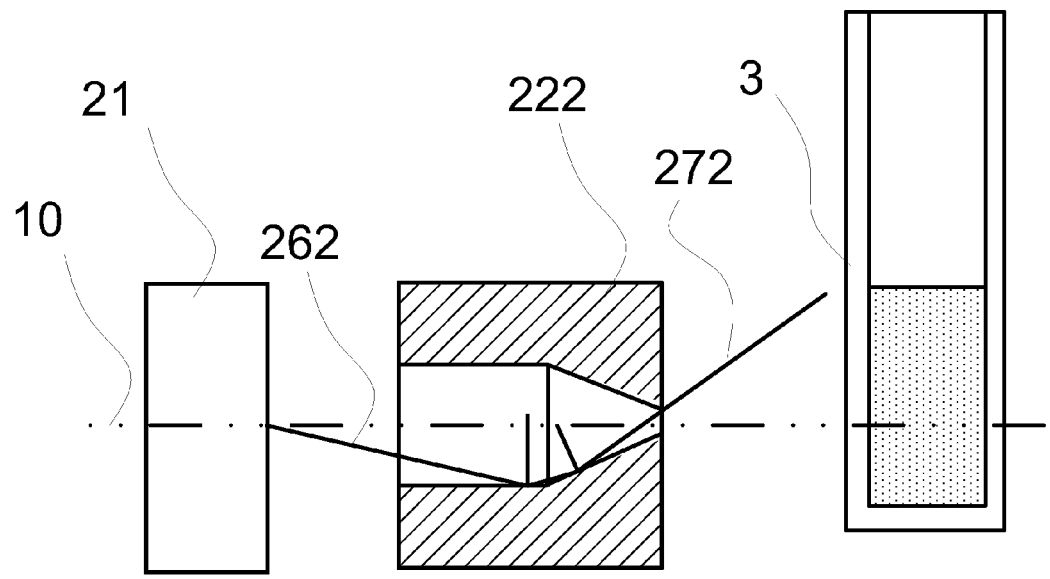
FIGS. 9-12 illustrates various embodiments of optical sample detection systems.

FIG. 9 illustrates another embodiment of the optical sample detection system. An internal surface of an optical stop 222 for stray light reduction includes a hybrid surface of a round tapered surface and a round cylindrical surface, which respectively are the round cylindrical surface and the round tapered surface along the direction of the optical axis. A light ray 262 emergent from a front optical component 21 is irradiated to the internal surface of the optical stop 222, and the reflected light ray is irradiated to the round tapered surface area of the optical stop through reflection of the round cylindrical surface of the optical stop. The internal surface of the optical stop includes the round tapered surface, so a deflection angle between an emergent light ray 272 after the reflection of the round tapered surface area and the optical axis 10 is larger, and a stray light emergent from the optical stop deviates from the area of a detected sample. Meanwhile, the deflection angle between the emergent light ray 272 and the optical axis 10 is larger, and the optical stop is made of an opaque material, so the reflection times of the stray light in the optical stop is increased, and the energy of the stray light is reduced during many times of reflection. The size of the round cylindrical surface and the taper of the round tapered surface need to be comprehensively determined according to practical parameters of the front and rear optical systems. The shapes and sizes of apertures of a large hole 24 and a small hole 25 of the optical stop for stray light reduction are determined according to practical optical designing requirements. The internal surface of the optical stop either may adopt a hybrid surface of a front round cylindrical surface and a rear round tapered surface, or may adopt a hybrid surface of a front round tapered surface and a rear round cylindrical surface.

On the basis of this embodiment, the round tapered surface of the internal surface of the optical stop for stray light reduction may be further deformed into a pyramidal surface, the round cylindrical surface of the internal surface of the optical stop for stray light reduction may be further deformed into a prismatic surface, and the optical stop for stray light reduction may be deformed into a hybrid surface of a round cylindrical surface and a pyramidal surface, or a hybrid surface of a prismatic surface and a round tapered surface, or a hybrid surface of a prismatic surface and a pyramidal surface. Likewise, the direction of the emergent stray light may be controlled, so that the emergent stray light deviates from the area of the detected sample, so as to increase the sample detection precision; meanwhile, by increasing the reflection times of the stray light in the optical stop, because the optical stop is made of an opaque material, the energy of the stray light is reduced after being reflected in the optical stop many times, and the sample detection precision may also be increased.

Figure 10:
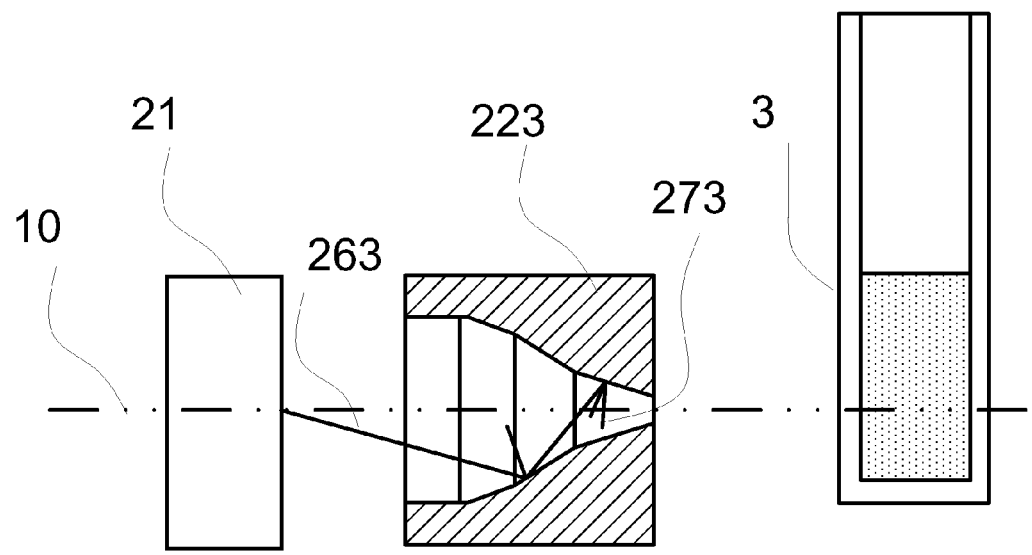

FIG. 10 illustrates another embodiment of the optical sample detection system for stray light reduction according to the present disclosure. An internal surface of an optical stop 223 for stray light reduction includes a hybrid surface of tapered surfaces of various different tapers. A light ray 263 emergent from a front optical component 21 is projected to the internal surface of the optical stop 223. Through the reflection action of the optical stop having the internal surface including the round tapered surface, it may be seen from the drawing that the deflection angle between a reflected light ray 273 after being reflected by the round tapered surface area many times and an optical axis 10 is larger, and the emergent stray light deviates from the area of a detected sample, so that the stray light cannot be incident to the rear optical system 23, so as to increase the sample detection precision. Because the deflection angle between the reflected light ray 273 after being reflected by the round tapered surface area many times and the optical axis 10 is larger, and the optical stop is made of an opaque material, the reflection times of the stray light in the optical stop is increased, the energy of the stray light is reduced during many times of reflection, and the sample detection precision may also be increased. The tapers or other size parameters of different round tapered surfaces are comprehensively determined according to characteristics of the incident light beam in different viewing fields and practical parameters of the rear optical component. The shapes and sizes of apertures of a large hole 24 and a small hole 25 of the optical stop for stray light reduction are determined according to practical optical designing requirements.

In one embodiment, the round tapered surface of the internal surface of the optical stop for stray light reduction may be further replaced with a pyramidal surface, or may further be a hybrid surface of a pyramidal surface and a round tapered surface, that is, as long as the stray light emergent from the optical stop deviates from the area of the detected sample, and the stray light does not enter the rear optical system, the sample detection precision may be increased. Meanwhile, by increasing the reflection times of the stray light in the optical stop, because the optical stop is made of an opaque material, and the energy of the stray light is reflected and reduced many times in the optical stop, the sample detection precision may be increased.

Figure 11:
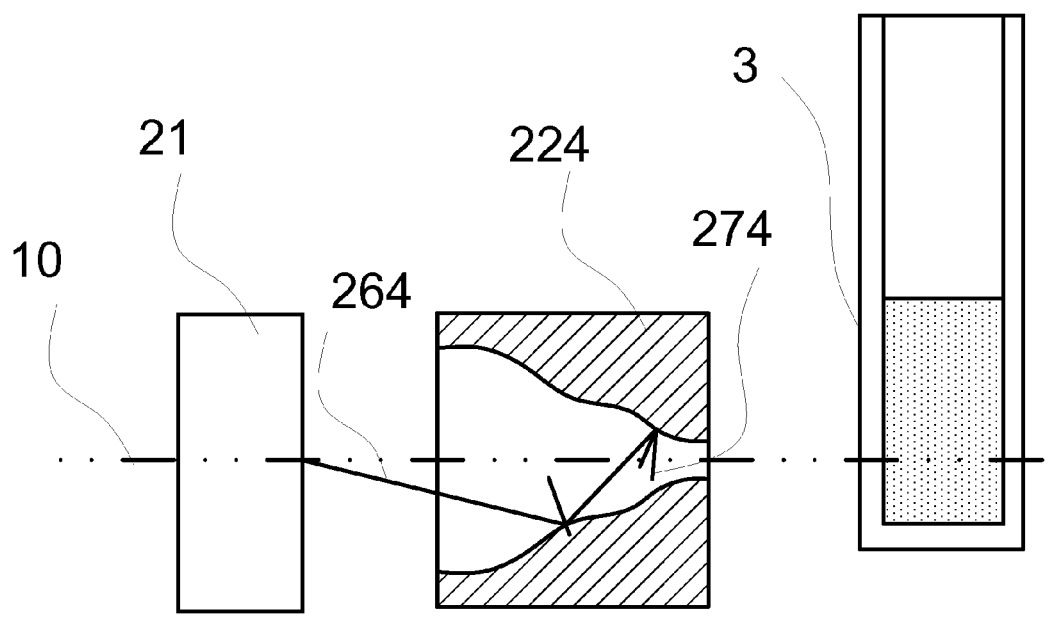

FIG. 11 illustrates another optical sample detection system according to an embodiment of the present disclosure. An internal surface of an optical stop 224 for stray light reduction includes a continuous smooth curved surface. A light ray 264 emergent from a front optical component 21 is irradiated to the optical stop 224, and through the reflection action of the optical stop 224 having the continuous smooth internal surface, a deflection angle between the light ray 274 after being reflected through the internal surface and the optical axis 10 is increased. In this way, an emergent light beam of the stray light upon many times of reflection deviates from the area of a detected sample, so as to prevent the stray light from entering the rear optical system, and increasing analysis precision of sample analysis. Because the deflection angle between the light ray 274 after being reflected through the internal surface and the optical axis 10 is increased, and the optical stop is made of an opaque material, the reflection times of the stray light in the optical stop is increased, the energy of the stray light is reduced during many times of reflection, and the sample detection precision may also be increased. The specific structure of the internal surface of the optical stop 224 is comprehensively determined according to characteristics of the incident light beam in different viewing fields and practical parameters of the rear optical component. The shapes and sizes of apertures of the large hole 24 and the small hole 25 of the optical stop for stray light reduction are determined according to practical optical designing requirements.

In various embodiments, in order to achieve a better effect of eliminating the stray light, the internal surface of the optical stop may be processed by roughness increasing, extinction paint spraying, or blackening. By further increasing the attenuation extent of the light beam incident to the internal surface of the optical stop for stray light reduction, the effect of eliminating the stray light is improved.

Figure 12:
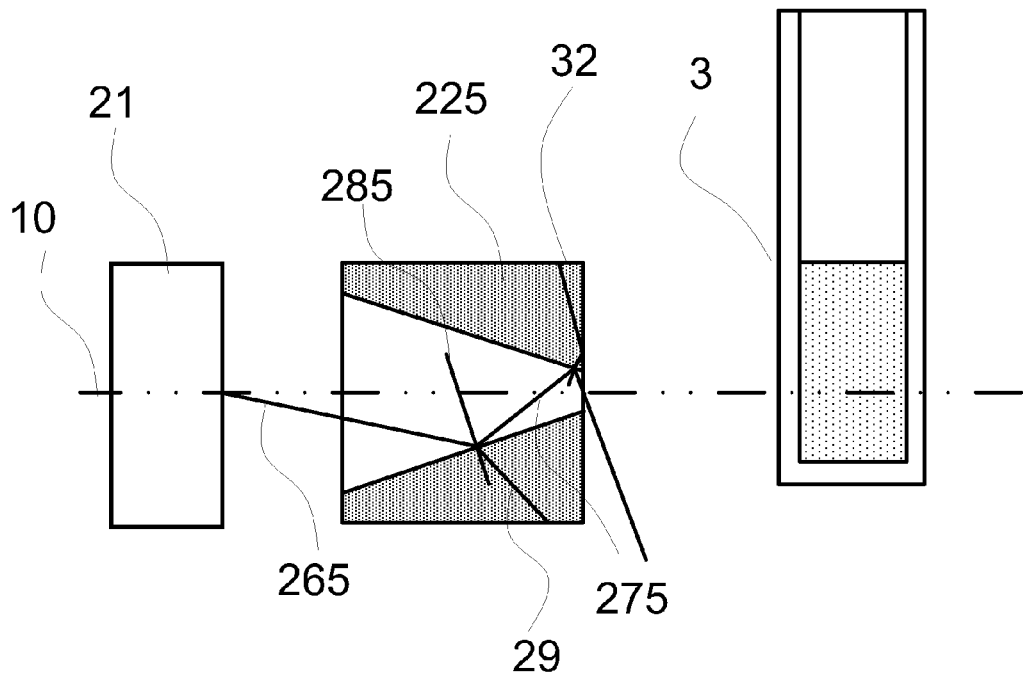

In one embodiment, in addition to making the stray light deviate from the detected sample with the reflection principle, refraction may further be used to eliminate the stray light. FIG. 12 illustrates another embodiment of the optical sample detection system. An optical stop for stray light reduction is made of a transparent material. A light ray 265 emergent from the front optical system 21 is irradiated to an internal surface of the transparent optical stop 225 for stray light reduction. The optical stop 225 is made of the transparent material, so the light ray is both reflected and refracted on an incident surface. A majority of the energy of the incident light ray is incident to the material with the refraction action. Due to the refraction action of the surface, the propagation direction of a refracted light ray 29 is deflected to a certain extent relative to the direction of the incident light ray 265. A refraction angle of the refracted light ray 29 is associated with an included angle between the incident light ray 265 and an incident surface normal 285. According to the optical refraction law, the product of the sine value of the included angle between the refracted light ray 29 and the incident surface normal 285 and the refractive index of the optical stop material is equal to the product of the sine value of the included angle between the incident light ray 265 and the incident surface normal 285 and the refractive index of an incident medium. The refractive index of the incident space is smaller than that of the optical stop material, so the included angle between the refracted light ray 29 and the incident surface normal 285 is smaller than the included angle between the incident light ray 265 and the incident surface normal 285.

If the surface where the refraction occurs is not specially processed, parts of the energy of the light rays are still reflected. The reflected light rays are still possibly incident to the rear optical system, thereby influencing the size of the light spot projected to the sample accommodation system. In order to reduce the reflected light ray 275 during the use of the transparent material, the optical stop structure in the above embodiment may be adopted, and by increasing the deflection angle of the reflected light ray 275 relative to the optical axis 10 of the optical system, the emergent light ray corresponding to the reflected light ray deviates from the area of the detected sample and/or times by which the reflected light ray is incident to the internal surface of the optical stop is increased, so as to increase the sample detection precision.

In one embodiment, the light ray refracted into the optical stop is very possibly incident to an external surface 32 of the optical stop. On the basis of this embodiment, in order to increase the attenuation action of the optical stop on the refracted light ray as much as possible, the external surface 32 of the optical stop is an external surface processed by roughness increasing, extinction paint spraying, and blackening; the material with strong absorption characteristic may further be used as the material of the optical stop, so that the refracted light ray is absorbed or scattered after being refracted into the transparent material; the internal surface may also be coated with an anti-reflective film, so that the light ray incident to the internal surface is not reflected as much as possible.

In a practical optical system, generally an optical stop fixing device is disposed out of the optical stop, and the optical stop fixing device is made of an opaque material, so that the refracted light ray incident to the optical stop is absorbed or scattered on the external surface of the optical stop. The capability of absorbing or scattering the light ray may also be increased through such solutions as roughness increasing, extinction paint spraying, and blackening processing on the surface of the optical stop fixing device. Meanwhile, by reasonably designing the internal surface structure of the optical stop for stray light reduction, it may be ensured that when the refracted light ray is incident to the interface of the optical stop and air, a majority of light rays satisfy the condition that the incident angle is larger than the total reflection angle, that is, the total reflection occurs on the interface where the refracted light ray is incident. In this way, the refracted light ray does not exit from the optical stop, thereby avoiding irradiating the stray light to the area of the detected sample, and increasing the sample detection precision. The specific internal surface structure of the optical stop for stray light reduction needs to be comprehensively considered and determined according to characteristics of the front and rear optical components, viewing field distribution of the incident light ray and extinction needs.

Although the invention has been disclosed above using various embodiments, they are not intended to be limiting. A skilled artisan can make various modifications and variations without departing from the scope of the invention. The scope of protection therefore falls within the appended claims.

What is claimed is:

1. An optical sample detection system, comprising:
   a light source;
   a convergence projection component configured for converging light rays emitted by the light source, the convergence projection component comprising:
      a front optical system;
      a rear optical system; and
      an optical stop disposed between the front and rear optical systems, wherein an angle between a normal of an internal surface of the optical stop and an optical axis in a light beam propagation direction is greater than 90° such that stray light incident to the internal surface of the optical stop is refracted away from the rear optical system;
   a sample accommodation component configured for accommodating a detected sample;
   a light beam collection component configured for receiving light rays carrying sample information from the sample accommodation component;
   a light splitting component configured for splitting polychromatic lights collected by the light beam collection component into independent spectrums or spectral bands; and
   a photoelectric detection component configured for receiving optical signals of different wavelengths separated through the light splitting component.

2. The optical sample detection system according to claim 1, wherein a front surface and a rear surface of the optical stop along the direction of the optical axis respectively correspond to a large hole and a small hole.

3. The optical sample detection system according to claim 1, wherein the internal surface of the optical stop at least comprises one tapered surface.

4. The optical sample detection system according to claim 1, wherein the internal surface of the optical stop at least comprises a hybrid surface of two tapered surfaces of different tapers.

5. The optical sample detection system according to claim 1, wherein the internal surface of the optical stop at least comprises a hybrid surface of a cylindrical surface and a tapered surface.

6. The optical sample detection system according to claim 1, wherein the internal surface of the optical stop at least comprises a continuous smooth curved surface.

7. The optical sample detection system according to claims 1, wherein the optical stop comprises an internal surface processed by roughness increasing, extinction paint spraying, or blackening.

8. The optical sample detection system according to claim 1, wherein the optical stop is made of a transparent material.

9. The optical sample detection system according to claim 8, wherein the optical stop has an internal surface coated with an anti-reflective film.

10. The optical sample detection system according to claim 8, wherein the optical stop comprises an external surface processed by roughness increasing, extinction paint spraying, or blackening.

* * * * *